US008889892B2

(12) United States Patent
Ohishi et al.

(10) Patent No.: US 8,889,892 B2
(45) Date of Patent: Nov. 18, 2014

(54) PROCESS FOR PRODUCING OLEFIN OXIDE

(75) Inventors: Yoshihiko Ohishi, Toyonaka (JP); Anusorn Seubsai, Los Angeles, CA (US); Selim Senkan, Los Angeles, CA (US)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/807,596

(22) PCT Filed: May 26, 2011

(86) PCT No.: PCT/US2011/038168
§ 371 (c)(1),
(2), (4) Date: Feb. 19, 2013

(87) PCT Pub. No.: WO2012/005822
PCT Pub. Date: Jan. 12, 2012

(65) Prior Publication Data
US 2013/0144074 A1 Jun. 6, 2013

Related U.S. Application Data

(60) Provisional application No. 61/362,978, filed on Jul. 9, 2010.

(51) Int. Cl.
*B01J 27/138* (2006.01)
*B01J 27/135* (2006.01)
*B01J 27/13* (2006.01)
*B01J 27/00* (2006.01)
*B01J 23/32* (2006.01)
*C07D 301/02* (2006.01)
*C07D 301/08* (2006.01)
*B01J 37/02* (2006.01)
*B01J 23/656* (2006.01)
*C07D 303/04* (2006.01)
*B01J 21/08* (2006.01)

(52) U.S. Cl.
CPC .............. *B01J 27/13* (2013.01); *C07D 301/08* (2013.01); *B01J 37/0201* (2013.01); *B01J 23/6562* (2013.01); *C07D 303/04* (2013.01); *B01J 21/08* (2013.01)
USPC ........... 549/523; 502/227; 502/230; 502/241; 502/324; 502/226

(58) Field of Classification Search
USPC .......... 549/523, 518; 502/226, 227, 230, 241, 502/324
See application file for complete search history.

(56) References Cited

U.S. PATENT DOCUMENTS

| 4,388,225 A | 6/1983 | Solomon |
| 5,112,795 A | 5/1992 | Minahan et al. |
| 5,958,824 A | 9/1999 | Rizkalla et al. |
| 6,362,349 B1 | 3/2002 | Kuperman et al. |
| 6,498,259 B1 | 12/2002 | Grey et al. |
| 6,765,101 B1 | 7/2004 | Bhasin et al. |
| 2003/0191328 A1* | 10/2003 | Jansen et al. .................. 549/533 |

FOREIGN PATENT DOCUMENTS

| CN | 1297443 A | 5/2001 |
| CN | 1429217 A | 7/2003 |
| CN | 1300125 C | 2/2007 |
| EP | 0 480 537 A1 | 10/1991 |
| JP | 2002-371074 A | 12/2002 |
| JP | 2002371074 * | 12/2002 |
| JP | 2004-531542 | 10/2004 |
| WO | WO2002/086102 A2 | 11/2002 |

OTHER PUBLICATIONS

International Search Report PCT/US2011/038168 dated Sep. 2, 2011.
Office Action received in U.S. Appl. No. 13/978,266 dated Oct. 2, 2013.
Official Action issued in counterpart Japanese Patent Application No. 2012-532153 dated Nov. 12, 2013, with English translation.
Office Action dated Jan. 21, 2014 received in Chinese Patent Application No. 201180033634.1 with full English translation).
Japanese Office Action dated Feb. 12, 2014 received in Japanese Application No. 2012-532153.
Office Action issued in the Chinese Patent Application No. 201180033634.1 dated Aug. 28, 2014.

* cited by examiner

*Primary Examiner* — Tayor Victor Oh
(74) *Attorney, Agent, or Firm* — Foley & Lardner LLP

(57) ABSTRACT

A process for producing an olefin oxide which comprises reacting an olefin with oxygen in the presence of a catalyst comprising (a) ruthenium metal or a ruthenium oxide, (b) manganese oxide and (c) alkaline metal component or alkaline earth metal component.

21 Claims, No Drawings

PROCESS FOR PRODUCING OLEFIN OXIDE

CROSS-REFERENCE TO RELATED APPLICATIONS

This application claims priority to and the benefit of U.S. Provisional Application No. 61/362, 978, filed Jul. 9, 2010, incorporated by reference here in its entirely.

TECHNICAL FIELD

The present invention relates to a process for producing an olefin oxide.

BACKGROUND ART

Olefin oxides, such as propylene oxide, are important and versatile intermediates used in the production of a large variety of valuable consumer products such as polyurethane foams, polymers, alkylene glycol, cosmetics, food emulsifiers and as fumigants and insecticides.

Previous research on olefin epoxidation involved the use of Ag-based catalysts (Appl. Catal. A. Gen. 2001, 221, 73.), as well as silica supported Cu (J. Catal. 2005, 236, 401), various metal oxides (Appl. Catal. A. Gen. 2007, 316, 142), Au-based catalysts with $H_2$ as a co-reactant (Ind. & Eng. Chem. Res. 1995, 34, 2298, J. Catal. 1998, 178, 566; Appl. Catal. A. Gen. 2000, 190, 43; Angew. Chem. Int. Ed. 2004, 43, 1546), titania based catalysts that deactivated quickly (Catal. Commun. 2001, 1356; Catal. Commun. 2003, 4, 385), molten salts of metal nitrates (Appl. Catal. A. Gen. 2000, 196, 217), the use of $O_3$ (Appl. Catal. A. Gen. 2000, 196, 217) and nitrous oxide (Ind. & Eng. Chem. Res. 1995, 34, 2298) as reactants. Although these developments are scientifically interesting, they have serious drawbacks, such as low PO selectivities and/or low propylene conversions, short catalyst lifetimes, the use of higher pressures or the use of costly co-reactants (Appl. Catal. A. Gen. 2007, 316, 142).

SUMMARY OF INVENTION

The present invention provides:

[1] A process for producing an olefin oxide which comprises reacting an olefin with oxygen in the presence of a catalyst comprising (a) ruthenium metal or ruthenium oxide, (b) manganese oxide and (c) alkaline metal component or alkaline earth metal component.

[2] The process according to [1], wherein the catalyst comprises (d) halogen component.

[3] The process according to [1] or [2], wherein the catalyst comprises (e) composite oxide.

[4] The process according to [1], wherein (a) ruthenium metal or ruthenium oxide, (b) manganese oxide and (c) alkaline metal component or alkaline earth metal component are supported on a porous support.

[5] The process according to [2], wherein (a) ruthenium metal or ruthenium oxide, (b) manganese oxide, (c) alkaline metal component or alkaline earth metal component and (d) halogen component are supported on a porous support.

[6] The process according to [4] or [5], wherein the porous support comprises $Al_2O_3$, $SiO_2$, $TiO_2$ or $ZrO_2$.

[7] The process according to [4] or [5], wherein the porous support comprises $SiO_2$.

[8] The process according to any one of [1] to [7], wherein the total amount of (a) ruthenium metal or ruthenium oxide, (b) manganese oxide and (c) alkaline metal component or alkaline earth metal component is 0.01 to 80% by weight of the amount of the catalyst.

[9] The process according to any one of [1] to [8], wherein the ruthenium/manganese metal molar ratio in the catalyst is 1/99 to 99/1.

[10] The process according to any one of [1] to [9], wherein the ruthenium/(c) component molar ratio in the catalyst is 1/99 to 99/1.

[11] The process according to any one of [1] to [10], wherein (a) ruthenium metal or ruthenium oxide is $RuO_2$.

[12] The process according to any one of [1] to [11], wherein (b) manganese oxide is $Mn_2O_3$.

[13] The process according to any one of [1] to [12], wherein (c) alkaline metal component or alkaline earth metal component is an alkaline metal-containing compound or an alkaline earth metal-containing compound.

[14] The process according to any one of [1] to [13], wherein (c) alkaline metal component or alkaline earth metal component is a sodium-containing compound.

[15] The process according to [4], wherein the catalyst is obtained by impregnating a porous support with a solution containing a ruthenium ion, a manganese ion and an alkaline metal or alkaline earth metal ion to prepare a composition, followed by calcining the composition.

[16] The process according to [5], wherein the catalyst is obtained by impregnating a porous support with a solution containing a ruthenium ion, a manganese ion, an alkaline metal or alkaline earth metal ion and a halogen ion to prepare a composition, followed by calcining the composition.

[17] The process according to any one of [1] to [16], wherein the olefin is propylene and the olefin oxide is propylene oxide.

[18] The process according to any one of [1] to [17], which comprises reacting an olefin with oxygen at a temperature of 100 to 350° C.

[19] A catalyst for production of an olefin oxide which comprises (a) ruthenium metal or ruthenium oxide, (b) manganese oxide and (c) alkaline metal component or alkaline earth metal component.

[20] The catalyst according to [19] which comprises (d) halogen component.

[21] The catalyst according to [19] or [20] which comprises (e) composite oxide.

[22] The catalyst according to [19], wherein (a) ruthenium metal or ruthenium oxide, (b) manganese oxide and (c) alkaline metal component or alkaline earth metal component are supported on a porous support.

[23] The catalyst according to [20], wherein (a) ruthenium metal or ruthenium oxide, (b) manganese oxide, (c) alkaline metal component or alkaline earth metal component and (d) halogen component are supported on a porous support.

[24] The catalyst according to [22] which is obtained by impregnating a porous support with a solution containing a ruthenium ion, a manganese ion and an alkaline metal or alkaline earth metal component to prepare a composition, followed by calcining the composition.

[25] The catalyst according to [23] which is obtained by impregnating a porous support with a solution containing a ruthenium ion, a manganese ion, an alkaline metal or alkaline earth metal component and a halogen ion to prepare a composition, followed by calcining the composition.

[26] The catalyst according to any one of [19] to [25], wherein (c) alkaline metal component or alkaline earth metal component is an alkaline metal-containing compound or an alkaline earth metal-containing compound.

[27] The catalyst according to any one of [22] to [26], wherein the porous support comprises $Al_2O_3$, $SiO_2$, $TiO_2$ or $ZrO_2$.

[28] The catalyst according to any one of [22] to [27], wherein the porous support comprises $SiO_2$.

[29] The catalyst according to any one of [19] to [28], wherein the olefin oxide is propylene oxide.

[30] Use of a catalyst for producing an olefin oxide, said catalyst comprising (a) ruthenium metal or ruthenium oxide, (b) manganese oxide and (c) alkaline metal component or alkaline earth metal component.

[31] The use of a catalyst according to [30], wherein the olefin oxide is propylene oxide.

DESCRIPTION OF EMBODIMENT

The process of the present invention comprises reacting an olefin with oxygen in the presence of a catalyst comprising (a) ruthenium metal or ruthenium oxide, (b) manganese oxide and (c) alkaline metal component or alkaline earth metal component.

The components (a), (b) and (c) may be supported on a porous support or a non-porous support. Examples of the non-porous support include a non-porous support comprising $SiO_2$ such as CAB-O-SIL (registered trademark).

In the catalyst, the components (a), (b) and (c) are preferably supported on a porous support. This catalyst is valuable for production of olefin oxides, which is one aspect of the present invention.

The porous support has pores capable of supporting the components (a), (b) and (c). The porous support comprises preferably $Al_2O_3$, $SiO_2$, $TiO_2$ or $ZrO_2$, more preferably $SiO_2$. Examples of the porous support comprising $SiO_2$ include mesoporous silica. Such a porous support may also comprise zeolites.

If the catalyst comprises $SiO_2$ as a support, olefin oxides can be prepared with good yield and good selectivity.

The catalyst may comprise one or more kinds of (a) ruthenium metal or ruthenium oxide. The ruthenium oxide is usually composed of ruthenium and oxygen. Examples of the ruthenium oxide include $RuO_2$ and $RuO_4$. The (a) component is preferably $RuO_2$.

The catalyst may comprise one or more kinds of (b) manganese oxide. The (b) manganese oxide is usually composed of manganese and oxygen. Examples of the (b) manganese oxide include MnO, $MnO_2$, $Mn_2O_3$ and $Mn_3O_4$. The manganese oxide is preferably $Mn_2O_3$ and $Mn_3O_4$.

The catalyst may comprise one or more kinds of (c) alkaline metal component or alkaline earth metal component.

The (c) component may be an alkaline metal-containing compound, an alkaline earth metal-containing compound, an alkaline metal ion or an alkaline earth metal ion.

Examples of the alkaline metal-containing compound include compounds containing an alkaline metal such as Na, K, Rb and Cs. Examples of the alkaline earth metal-containing compound include compounds containing an alkaline earth metal such as Ca, Mg, Sr and Ba. Examples of the alkaline metal ion include $Na^+$, $K^+$, $Rb^+$ and $Cs^+$. Examples of the alkaline earth metal ion include $Ca^{2+}$, $Mg^{2+}$, $Sr^{2+}$ and $Ba^{2+}$.

The alkaline metal component may be an alkaline metal oxide. Examples of the alkaline metal oxide include $Na_2O$, $Na_2O_2$, $K_2O$, $KO_2$, $K_2O_2$, $Rb_2O$, $Rb_2O_2$, $Cs_2O$, $Cs_2O_2$, $CsO_2$, $CsO_3$, $Cs_2O_3$, $Cs_{11}O_3$, $Cs_4O$ and $Cs_7O$. The alkaline earth metal component may be alkaline metal earth oxide.

Examples of the alkaline earth metal oxide include CaO, $CaO_2$, MgO, $MgO_2$, SrO, $SrO_2$, BaO and $BaO_2$.

The alkaline metal-containing compound is preferably an alkaline metal salt. The alkaline earth metal-containing compound is preferably an alkaline earth metal salt. The alkaline metal salt comprises the alkaline metal ion as mentioned above with an anion. The alkaline earth metal salt comprises the alkaline earth metal ion as mentioned above with an anion. Examples of anions in such salts include $F^-$, $Cl^-$, $Br^-$, $I^-$, $OH^-$, $NO_3^-$, $SO_4^{2-}$, $CO_3^{2-}$, $HCO_3^-$ and $SO_3^{2-}$. Such salts are preferably an alkaline metal salt with a halogen, such as an alkaline metal halide, or an alkaline earth metal-containing salt with a halogen, such as an alkaline earth metal halide, more preferably an alkaline metal salt with a halogen, still more preferably an alkaline metal chloride.

The (c) component is preferably an alkaline metal-containing compound or alkaline earth metal-containing compound, more preferably a sodium-containing compound.

The catalyst comprises preferably $RuO_2$, any of $Mn_2O_3$ and $Mn_3O_4$ and an alkaline metal-containing salt, still more preferably $RuO_2$, any of $Mn_2O_3$ and $Mn_3O_4$ and a sodium-containing salt, because the olefin oxide yield and selectivity can be improved by adopting such a combination to the production of an olefin oxide. Particularly if the catalyst comprises NaCl as the (c) component, it can show excellent olefin oxide selectivity.

The ruthenium/manganese metal molar ratio in the catalyst is preferably 1/99 to 99/1. When the metal molar ratio falls within such a range, the olefin oxide yield and selectivity can be further improved. The lower limit of the molar ratio is more preferably 2/98, still more preferably 3/97, further preferably 10/90, particularly preferably 20/80. The upper limit of the molar ratio is more preferably 98/2, still more preferably 97/3, further preferably 90/10, particularly preferably 80/20.

The ruthenium/(c) component metal molar ratio in the catalyst is preferably 1/99 to 99/1. When the molar ratio falls within such a range, the olefin oxide yield and selectivity can be further improved. The lower limit of the molar ratio is more preferably 2/98, still more preferably 3/97. The upper limit of the molar ratio is more preferably 98/2, still more preferably 97/3. The "(c) component" of the molar ratio represents the alkaline metal or alkaline earth metal existing in the (c) component and the alkaline metal or alkaline earth metal ion existing in the (c) component.

When the components (a), (b) and (c) are supported on a porous support in the catalyst, the total content of the components (a), (b) and (c) is preferably 0.01 to 80% by weight of the amount of the catalyst. When the total content falls within such a range, the olefin oxide yield and selectivity can be further improved. The lower limit of the total content is more preferably 0.05% by weight, still more preferably 0.1% by weight of the amount of the catalyst. The upper limit of the total content is more preferably 50% by weight, still more preferably 30% by weight of the amount of the catalyst.

The catalyst may comprise (d) halogen component besides the components (a), (b) and (c). The component (d) is generally a halogen-containing compound. Examples of the halogen include chlorine, fluorine, iodine and bromine.

Examples of such a halogen-containing compound include ruthenium halides such as $RuCl_3$, manganese halides such as $MnCl_2$ and $MnCl_3$, ruthenium oxyhalides such as $Ru_2OCl_4$, $Ru_2OCl_5$ and $Ru_2OCl_6$, and manganese oxyhalides such as $MnOCl_3$, $MnO_2Cl_2$, $MnO_3Cl$ and $Mn_8O_{10}Cl_3$ preferably $Mn_8O_{10}Cl_3$.

The component (d) may be supported on any of the components (a), (b) and (c) or the porous support.

The catalyst may comprise (e) composite oxides, including those composed of ruthenium, manganese and oxygen, those composed of sodium, manganese and oxygen, such as $NaMnO_2$, and those composed of sodium, ruthenium and oxygen, such as $NaRuO_4$ and $Na_4RuO_4$.

If the catalyst comprises the component (d) or (e), the component may be supported on the porous support as mentioned above.

Production of the catalyst is not restricted to a specific process, examples of which include the conventional methods.

When the components (a), (b) and (c) are supported on a porous support in the catalyst, the catalyst can be obtained by impregnating a porous support with a solution containing a ruthenium ion, a manganese ion and an alkaline metal or alkaline earth metal ion to prepare a composition, followed by calcining the composition. The support can be in form of powder, or shaped to a desired structure as necessary. If the catalyst comprises component (c) which is an alkaline metal salt with a halogen or alkaline earth metal salt with a halogen, and/or the component (d) supported on the porous support, the catalyst can be obtained in the same procedure as mentioned above except that solution contains a manganese ion, a ruthenium ion, an alkaline metal or alkaline earth metal-containing ion and a halogen ion.

The solution containing a ruthenium ion, a manganese ion and an alkaline metal or alkaline earth metal ion can be prepared by dissolving a ruthenium metal salt or a ruthenium oxide, a manganese metal salt or a manganese oxide, and an alkaline metal or alkaline earth metal salt or an alkaline metal or alkaline earth metal oxide in a solvent. The solution is preferably prepared by dissolving a ruthenium metal salt, a manganese metal salt and an alkaline metal or alkaline earth metal salt in a solvent. Examples of the ruthenium metal salt include, for example, a halide such as ruthenium bromide, ruthenium chloride, ruthenium iodide, an oxyhalide such as $Ru_2OCl_4$, $Ru_2OCl_5$ and $Ru_2OCl_6$, a halogeno complex such as $[RuCl_2(H_2O)_4]Cl$, an ammine complex such as $[Ru(NH_3)_5 H_2O]Cl_2$, $[Ru(NH_3)_5Cl]Cl_2$, $[Ru(NH_3)_6]Cl_2$ and $[Ru(NH_3)_6]Cl_3$, a carbonyl complex such as $Ru(CO)_5$ and $Ru_a(CO)_{12}$, a carboxylate complex such as $[Ru_3O(OCOCH_3)_6(H_2O)_3]$ ruthenium nitrosylchloride, and $[Ru_2(OCOR)_4]Cl$ (R=alkyl group having 1 to 3 carbon atoms), a nitrosyl complex such as $[Ru(NH_3)_5(NO)]Cl_3$, $[Ru(OH)(NH_3)_4(NO)](NO_3)_2$ and $[Ru(NO)](NO_3)_3$, an amine complex, an acetylacetonate complex, and an ammonium salt such as $(NH_4)_2RuCl_6$. Examples of the manganese metal salt include manganese carbonate, manganese nitrate, manganese sulfate, manganese bromide, manganese chloride, manganese iodide, manganese perchlorate, manganese acetate, and manganese acetylacetonate. The alkaline metal or alkaline earth metal salt for the solution may be the same as or different from the (c) component. Examples of the alkaline metal or alkaline earth metal salt include alkaline metal nitrates, alkaline earth metal nitrates, alkaline metal halides, alkaline earth metal halides, alkaline metal acetates, alkaline earth metal acetates, alkaline metal butyrates, alkaline earth metal butyrates, alkaline metal benzoates, alkaline earth metal benzoates, alkaline metal alkoxides, alkaline earth metal alkoxides, alkaline metal carbonates, alkaline earth metal carbonates, alkaline metal citrates, alkaline earth metal citrates, alkaline metal formates, alkaline earth metal formates, alkaline metal hydrogen carbonates, alkaline earth metal hydrogen carbonates, alkaline metal hydroxides, alkaline earth metal hydroxides, alkaline metal hypochlorites, alkaline earth metal hypochlorites, alkaline metal halates, alkaline earth metal halates, alkaline metal nitrites, alkaline earth metal nitrites, alkaline metal oxalates, alkaline earth metal oxalates, alkaline metal perhalates, alkaline earth metal perhalates, alkaline metal propionates, alkaline earth metal propionates, alkaline metal tartrates and alkaline earth metal tartrates, preferably alkaline metal halides and alkaline metal nitrates, more preferably $NaNO_3$ and NaCl. At least one of the metal salts for the solvent contains preferably a halogen ion, more preferably a chloride ion. Such a halogen ion may form the components (c) such as alkaline metal halides and alkaline earth metal halides, or the (d) components such as ruthenium halides, ruthenium oxyhalides, manganese halides and manganese oxyhalides.

The solution may contain acidic or basic compounds in order to control its pH.

Examples of the solvent for the solution include water and alcohols such as methanol or ethanol.

The total amount of the porous support is preferably 20 to 99.99% by weight, more preferably 50 to 99.95% by weight, still preferably 70 to 99.9% by weight of the catalyst as obtained.

The composition as prepared by the impregnation is usually dried, and the drying method thereof is not limited.

The composition as prepared by the impregnation is preferably dried at a temperature of approximately 40° C. to approximately 200° C. before calcining the composition. Drying is preferably performed under an atmosphere of air or also under an inert gas atmosphere (for example, Ar, $N_2$, He) at standard pressure or reduced pressure. A drying time is preferably in the range from 0.5 to 24 hours. After drying, the composition can be shaped to a desired structure as necessary.

The method of calcining the composition is not limited, and calcining the composition is preferably performed under a gas atmosphere containing oxygen. Examples of such a gas stream include air, oxygen, nitrous oxide and other oxidizing gases. The gas may be used after being mixed at an appropriate ratio with a diluting gas such as nitrogen, helium, argon, and water vapor. An optimal temperature for calcination varies depending on the kind of the gas and the composition, however, a too high temperature may cause agglomeration of manganese oxide and ruthenium oxide. Accordingly, the calcination temperature is typically 200 to 800° C., preferably at 400 to 600° C.

The catalyst can be used as powder, but it is usual to shape it into desired structures such as spheres, pellets, cylinders, rings, hollow cylinders, or stars. The catalyst can be shaped by a known procedure such as extrusion, ram extrusion, tableting. The calcination is normally performed after shaping into the desired structures, but it can also be performed before shaping them.

Next, the following explains a reaction of an olefin with oxygen in the presence of the catalyst as described above.

In the present invention, the olefin may have a linear or branched structure and contains usually 2 to 10, preferably 2 to 8 carbon atoms. Examples of the olefin include preferably ethylene, propylene, butene, pentene, hexene, heptene, octene, and butadiene, more preferably ethylene, propylene and butene, still more preferably propylene.

The reaction is generally performed in the gas phase. In the reaction, the olefin and oxygen may be fed respectively in the form of gas. Olefin and oxygen gases can be fed in the form of their mixed gas. Olefin and oxygen gases may be fed with diluent gases. Examples of diluent gases include nitrogen, rare gases such as argon and helium, carbon dioxide, water vapor, methane, ethane and propane. Preferable diluent gases are nitrogen, carbon dioxide and the both thereof.

As the oxygen source, pure oxygen may be used, or a mixed gas containing pure oxygen and a gas inactive to the reaction, such as air, may be used. Examples of the gas inactive to the reaction include nitrogen, rare gases such as argon and helium, carbon dioxide, water vapor, methane, ethane and propane. Preferable gases inactive to the reaction are nitrogen, carbon dioxide and the both thereof. The amount of oxygen used varies depending on the reaction type, the catalyst, the reaction temperature or the like. The amount of oxygen is typically 0.01 to 100 mol, and preferably 0.03 to 30 mol, more preferably 0.05 to 10 mol and especially preferably 0.25 to 10 mol, with respect to 1 mol of the olefin.

The reaction is performed at a temperature generally of 100 to 350° C., preferably of 120 to 330° C., more preferably of 170 to 310° C.

The present reaction is carried out under the reaction pressure in the range of the reduced pressure to the increased pressure. By carrying out the reaction under such a reaction pressure condition, the productivity and selectivity of olefin oxides can be improved. The reduced pressure means a pressure lower than an atmospheric pressure. The increased pressure means a pressure higher than an atmospheric pressure. The reaction pressure is typically in the range of 0.01 to 3 MPa, and preferably in the range of 0.02 to 2 MPa, in the absolute pressure.

The reaction of the present invention may be carried out as a batch reaction or a continuous reaction, preferably as a continuous reaction for industrial application. The reaction of the present invention may be carried out by mixing an olefin and oxygen and then contacting the mixture with the catalyst under the reduced pressure to the increased pressure.

The reactor type is not limited. Examples of the reactor types are fluid bed reactor, fixed bed reactor, moving bed reactor, and the like, preferably fixed bed reactor. In the case of using fixed bed reactor, single tube reactor or multi tube reactor can be employed. More than one reactors can be used. If the number of reactors is large, small reactors as for example microreactors, can be used, which can have multiple channels. Adiabatic type or heat exchange type may be also used.

In the present invention, the olefin oxide may have a linear or branched structure and contains usually 2 to 10, preferably 2 to 8 carbon atoms. Examples of the olefin oxides include preferably ethylene oxide, propylene oxide, butene oxide, pentene oxide, hexene oxide, heptene oxide, octene oxide, and 3,4-epoxy-1-butene, more preferably ethylene oxide, propylene oxide and butene oxide, still more preferably propylene oxide.

The olefin oxide as obtained can be collected by a method known in the art such as separation by distillation.

EXAMPLES

In Example 1, data analysis was performed according to the following method:

A reaction gas was mixed with ethane (10 Nml/min) as an external standard, and then directly introduced in the TCD-GC equipped with a column of Gaskuropack 54 (2 m). All products in the reaction gas were collected for 1 hour with double methanol traps connected in series and cooled with a dry-ice/methanol bath. The two methanol solutions were mixed together and added to anisole as an external standard, and then analyzed with two FID-GCs quipped with different columns, PoraBOND U (25 m) and PoraBOND Q (25 m).

The detected products were propylene oxide (PO), acetone (AT), $CO_x$ ($CO_2$ and CO), propanal (PaL), acrolein (AC).

The propylene conversion, product selectivity, and yield (calculated as selectivity of product×propylene conversion) of products were calculated on the basis of carbon balance. Propylene conversions ($X_{PR}$) were determined from the following:

$$X_{PR} = \{[PO+AC+AT+PaL+CO_2/3]_{out}/[C_3H_6]_{in}\} \times 100\%;$$

and PO selectivities ($S_{PO}$) were then calculated using the following expression:

$$S_{PO} = \{[PO]/[PO+AC+AT+PaL+CO_2/3]\} \times 100\%$$

Each metal weight was determined from the amounts of the metal salts used for preparation of the catalyst.

Example 1

Catalysts were prepared by co-impregnation method. This was accomplished by the parallel co-impregnation of a pre-determined weight (1.9 g) of amorphous silica powder ($SiO_2$, Japan Aerosil, 380 m$^2$/g) by an aqueous solution mixture containing 0.55 g of $(NH_4)_2RuCl_6$ (Aldrich), 0.28 g of $MnCl_2$ and 0.10 g of NaCl (Wako). The aqueous solution mixture was allowed to impregnate the support with stirring for 24 hour in the air. The resulting materials were then heated at 100° C. until dried, and calcined at 500° C. for 12 hours in the air.

The catalysts were evaluated by using a fixed-bed reactor. Filling a ½-inch OD reaction tube made of stainless steel with 1 mL of the thus obtained catalyst, the reaction tube was supplied with 450 NmL/h of propylene, 900 NmL/h of the air, 990 NmL/h of a nitrogen gas to carry out the reaction at the reaction temperature of 200, 250 and 270° C. under the condition of the increased pressure (equivalent to 0.3 MPa in the absolute pressure).

The result is shown in Table 1.

TABLE 1

| Example | 1 | | |
|---|---|---|---|
| Total metal loading (wt %) | 12.5 | | |
| Mn/Ru/Na (weight ratio of metal) | 4/2/1 | | |
| Reaction temperature (° C.) | 200 | 250 | 270 |
| Propylene conversion (%) | 0.6 | 6.4 | 7.1 |
| Propylene oxide selectivity (%) | 20 | 6 | 12 |

Example 2

The catalyst obtained in Example 1 (5.0 mg) was placed in a well of a reactor as mentioned in Angew. Chem. Int. Ed. 38 (1999) 2794, equipped with array microreactors, wells along each reactor channel and a passivated 200 micron ID capillary sampling probe within the reactor channel. The mixture gas consisting of 1 vol % propylene ($C_3H_6$), 4 vol % $O_2$, and 95 vol % He was fed to the well containing the catalyst, at a gas hourly space velocity (GHSV) of 20,000 h$^{-1}$, at a reactor temperature of 250° C.

Gas sampling was accomplished by withdrawing reactor exit gases using the passivated 200 micron ID capillary sampling probe.

Data analysis for sample gases was conducted by an on-line Micro-Gas Chromatograph (Varian, CP-4900) equipped with a thermal conductivity detector (TCD), PoraPLOT U (10M) and Molecular sieve 13X (10M).

The detected products were propylene oxide (PO), acetone (AT), acetaldehyde (AD), $CO_x$ ($CO_2$ and CO), and propanal+acrolein (PaL+AC).

The propylene conversion, product selectivity, and yield (calculated as selectivity of product×propylene conversion) of products were calculated on the basis of carbon balance. Propylene conversions ($X_{PR}$) were determined from the following:

$$X_{PR} = \{[PO+AC+AT+2AD/3+CO_2/3]_{out}/[C_3H_6]_{in}\} \times 100\%;$$

and PO selectivities ($S_{PO}$) were then calculated using the following expression:

$$S_{PO} = \{[PO]/[PO+AC+AT+2AD/3+CO_2/3]\} \times 100\%$$

Note: PaL+AC are reported together since the two compounds appear at the same retention time, although the PaL is typically only found in trace amounts.

The results are shown in Table 2.

TABLE 2

| Example | 2 |
|---|---|
| Reaction temperature (° C.) | 250 |
| Propylene conversion (%) | 3.7 |
| Propylene oxide selectivity (%) | 32 |

The invention claimed is:

1. A process for producing an olefin oxide which comprises reacting an olefin with oxygen in the presence of a catalyst comprising (a) ruthenium metal or a ruthenium oxide, (b) manganese oxide and (c) alkaline metal component or alkaline earth metal component,
    wherein the ruthenium/manganese metal ratio in the catalyst is 10/90 to 97/3, and
    wherein the reaction is performed at a temperature of 250 to 350° C.

2. The process according to claim 1, wherein the catalyst comprises (d) halogen component.

3. The process according to claim 1 or 2, wherein the catalyst comprises (e) composite oxide.

4. The process according to claim 1, wherein (a) ruthenium metal or a ruthenium oxide, (b) manganese oxide and (c) alkaline metal component or alkaline earth metal component are supported on a porous support.

5. The process according to claim 2, wherein (a) ruthenium metal or a ruthenium oxide, (b) manganese oxide, (c) alkaline metal component or alkaline earth metal component and (d) halogen component are supported on a porous support.

6. The process according to claim 4 or 5, wherein the porous support comprises $Al_2O_3$, $SiO_2$, $TiO_2$ or $ZrO_2$.

7. The process according to claim 4 or 5, wherein the porous support comprises $SiO_2$.

8. The process according to claim 1 or 2, wherein the total amount of (a) ruthenium metal or a ruthenium oxide, (b) manganese oxide and (c) alkaline metal component or alkaline earth metal component is 0.01 to 80% by weight of the amount of the catalyst.

9. The process according to claim 1 or 2, wherein the ruthenium/(c) component molar ratio in the catalyst is 1/99 to 99/1.

10. The process according to claim 1 or 2, wherein (a) ruthenium metal or ruthenium oxide is $RuO_2$.

11. The process according to claim 1 or 2, wherein (b) manganese oxide is $Mn_2O_3$.

12. The process according to claim 1 or 2, wherein (c) alkaline metal component or alkaline earth metal component is an alkaline metal-containing compound or an alkaline earth metal-containing compound.

13. The process according to claim 1 or 2, wherein (c) alkaline metal component or alkaline earth metal component is a sodium-containing compound or a potassium-containing compound.

14. The process according to claim 4, wherein the catalyst is obtained by impregnating a porous support with a solution containing a ruthenium ion, a manganese ion and an alkaline metal or alkaline earth metal ion to prepare a composition, followed by calcining the composition.

15. The process according to claim 5, wherein the catalyst is obtained by impregnating a porous support with a solution containing a ruthenium ion, a manganese ion, an alkaline metal or alkaline earth metal ion and a halogen ion to prepare a composition, followed by calcining the composition.

16. The process according to claim 1 or 2, wherein the olefin is propylene and the olefin oxide is propylene oxide.

17. The process according to claim 1, wherein the ruthenium/manganese metal molar ratio in the catalyst is 20/80 to 97/3.

18. The process according to claim 1, wherein the ruthenium/manganese metal molar ratio in the catalyst is 20/80 to 90/10.

19. The process according to claim 9, wherein the ruthenium/(c) component molar ratio in the catalyst is 2/98 to 98/2.

20. The process according to claim 9, wherein the ruthenium/(c) component molar ratio in the catalyst is 3/97 to 97/3.

21. The process according to claim 1, wherein (a) ruthenium metal or the ruthenium oxide comprises $RuO_2$.

* * * * *